(12) United States Patent
Mosley

(10) Patent No.: US 6,231,558 B1
(45) Date of Patent: May 15, 2001

(54) SANITARY UNDERGARMENT

(76) Inventor: Sheila Mosley, P.O. Box 447, Prague, OK (US) 74864

(*) Notice: Subject to any disclaimer, the term of this patent is extended or adjusted under 35 U.S.C. 154(b) by 0 days.

(21) Appl. No.: 09/150,609

(22) Filed: Sep. 10, 1998

(51) Int. Cl.[7] .................................................. A61F 13/15
(52) U.S. Cl. .............................. 604/385.29; 604/385.3; 604/396
(58) Field of Search .......... 604/385.101, 385.21–385.3, 604/886, 393–396, 400–402

(56) References Cited

U.S. PATENT DOCUMENTS

| | | | |
|---|---|---|---|
| 979,730 | * 12/1910 | Argo | 604/401 |
| 2,627,858 | * 2/1953 | Miller | 604/386 |
| 2,954,770 | * 10/1960 | Roth | 604/396 |
| 4,619,649 | * 10/1986 | Roberts . | |
| 4,695,278 | * 9/1987 | Lawson | 604/385.2 |
| 5,366,453 | * 11/1994 | Zehner et al. | 604/393 |
| 5,575,782 | * 11/1996 | Hasse et al. | 604/396 |
| 5,745,922 | * 5/1998 | Rajala et al. | 604/385.2 |

FOREIGN PATENT DOCUMENTS

| | | | |
|---|---|---|---|
| 2 253 131 | * 9/1992 | (GB) | 604/385.2 |
| 5-192366 | * 8/1993 | (JP) | 604/396 |

* cited by examiner

Primary Examiner—Aaron J. Lewis
Assistant Examiner—K. M. Reichle

(57) ABSTRACT

A sanitary undergarment for providing a disposable undergarment to protect a female user during menstruation. The garment includes an undergarment having front and back portions, a pair of side portions, a crotch portion, a waist opening and a pair of leg openings. The undergarment has an upper region extending around the front, back, and side portions of the undergarment adjacent the outer periphery of the waist opening. The undergarment also has a middle region extending around the front, back, and side portions of the undergarment adjacent the upper region. The middle region includes a resiliently elastic material adapted for constricting the middle region around a wearer. The undergarment has a lower region beneath the middle region in which the crotch portion and the leg openings are located. The lower region includes a substantially water impermeable material for preventing the passage of menstrual fluids therethrough between the inside and outside of the undergarment. The crotch region has a primary absorbing pad on the inside of the undergarment. The undergarment also has a secondary absorbing pad on the primary absorbing pad.

1 Claim, 2 Drawing Sheets

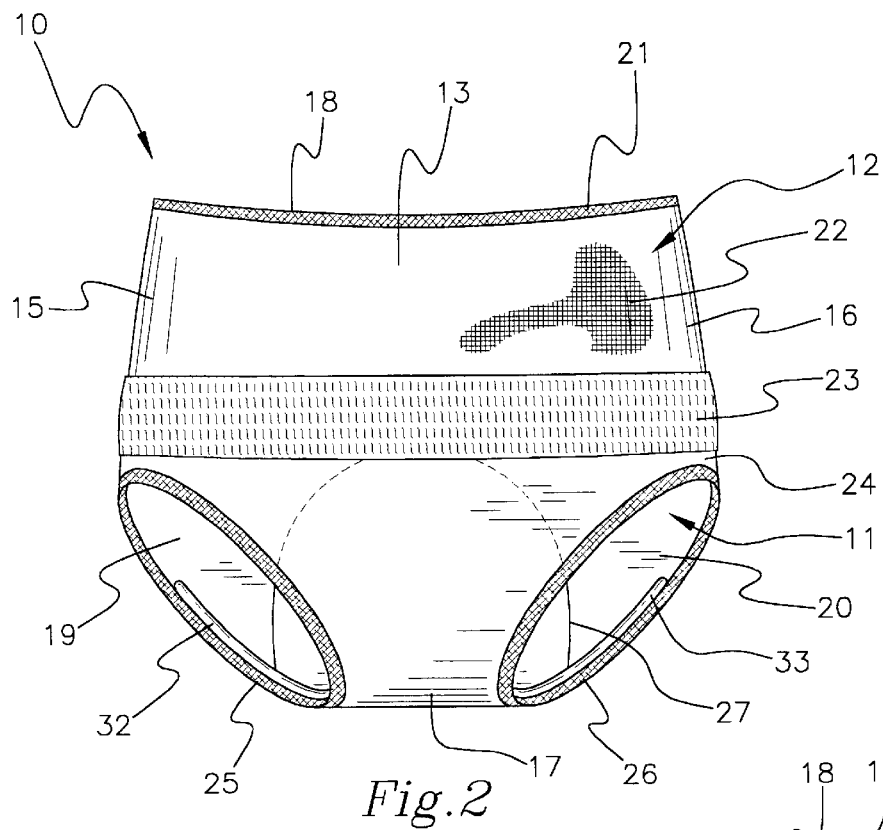
Fig.2
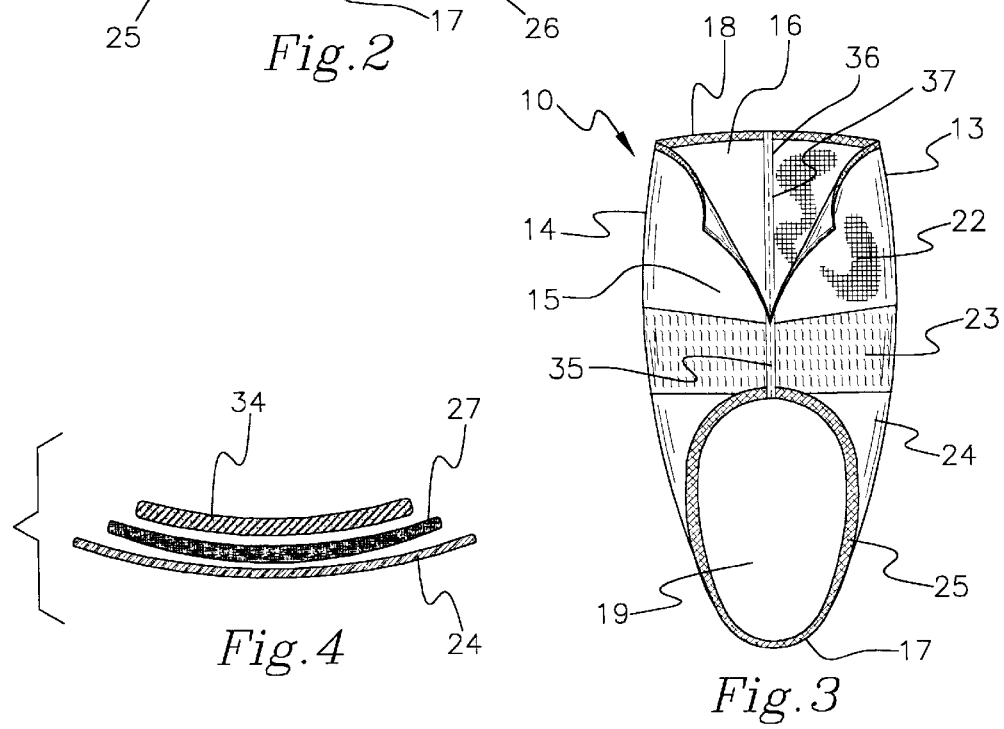
Fig.4
Fig.3

US 6,231,558 B1

SANITARY UNDERGARMENT

BACKGROUND OF THE INVENTION

1. Field of the Invention

The present invention relates to sanitary undergarments and more particularly pertains to a new sanitary undergarment for providing a disposable undergarment to protect a female user during menstruation.

2. Description of the Prior Art

The use of sanitary undergarments is known in the prior art.

Known prior art sanitary undergarments include U.S. Pat. Nos. 4,560,381; 2,102,359; 3,232,293; 3,420,236; U.S. Pat. No. Des. 330,590; and U.S. Pat. No. 4,940,463.

While these devices fulfill their respective, particular objectives and requirements, the aforementioned patents do not disclose a new sanitary undergarment. The inventive device includes an undergarment having front and back portions, a pair of side portions, a crotch portion, a waist opening and a pair of leg openings. The undergarment has an upper region extending around the front, back, and side portions of the undergarment adjacent the outer periphery of the waist opening. The undergarment also has a middle region extending around the front, back, and side portions of the undergarment adjacent the upper region. The middle region comprises a resiliently elastic material adapted for constricting the middle region around a wearer. The undergarment has a lower region beneath the middle region in which the crotch portion and the leg openings are located. The lower region comprises a substantially water impermeable material for preventing the passage of menstrual fluids therethrough between the inside and outside of the undergarment. The crotch region has a primary absorbing pad on the inside of the undergarment. The undergarment also has a secondary absorbing pad on the primary absorbing pad.

In these respects, the sanitary undergarment according to the present invention substantially departs from the conventional concepts and designs of the prior art, and in so doing provides an apparatus primarily developed for the purpose of providing a disposable undergarment to protect a female user during menstruation.

SUMMARY OF THE INVENTION

In view of the foregoing disadvantages inherent in the known types of sanitary undergarments now present in the prior art, the present invention provides a new sanitary undergarment construction wherein the same can be utilized for providing a disposable undergarment to protect a female user during menstruation.

To attain this, the present invention generally comprises an undergarment having front and back portions, a pair of side portions, a crotch portion, a waist opening and a pair of leg openings. The undergarment has an upper region extending around the front, back, and side portions of the undergarment adjacent the outer periphery of the waist opening. The undergarment also has a middle region extending around the front, back, and side portions of the undergarment adjacent the upper region. The middle region comprises a resiliently elastic material adapted for constricting the middle region around a wearer. The undergarment has a lower region beneath the middle region in which the crotch portion and the leg openings are located. The lower region comprises a substantially water impermeable material for preventing the passage of menstrual fluids therethrough between the inside and outside of the undergarment. The crotch region has a primary absorbing pad on the inside of the undergarment. The undergarment also has a secondary absorbing pad on the primary absorbing pad.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The abstract is neither intended to define the invention of the application, which is measured by the claims, nor is it intended to be limiting as to the scope of the invention in any way.

It is another object of the present invention to provide a new sanitary undergarment which may be easily and efficiently manufactured and marketed.

It is a further object of the present invention to provide a new sanitary undergarment which is of a durable and reliable construction.

An even further object of the present invention is to provide a new sanitary undergarment which is susceptible of a low cost of manufacture with regard to both materials and labor, and which accordingly is then susceptible of low prices of sale to the consuming public, thereby making such sanitary undergarment economically available to the buying public.

Still yet another object of the present invention is to provide a new sanitary undergarment which provides in the apparatuses and methods of the prior art some of the advantages thereof, while simultaneously overcoming some of the disadvantages normally associated therewith.

Still another object of the present invention is to provide a new sanitary undergarment for providing a disposable undergarment to protect a female user during menstruation.

Yet another object of the present invention is to provide a new sanitary undergarment which includes an undergarment having front and back portions, a pair of side portions, a crotch portion, a waist opening and a pair of leg openings. The undergarment has an upper region extending around the front, back, and side portions of the undergarment adjacent the outer periphery of the waist opening. The undergarment also has a middle region extending around the front, back, and side portions of the undergarment adjacent the upper region. The middle region comprises a resiliently elastic material adapted for constricting the middle region around a wearer. The undergarment has a lower region beneath the middle region in which the crotch portion and the leg openings are located. The lower region comprises a substantially water impermeable material for preventing the passage of menstrual fluids therethrough between the inside and outside of the undergarment. The crotch region has a primary absorbing pad on the inside of the undergarment. The undergarment also has a secondary absorbing pad on the primary absorbing pad.

Still yet another object of the present invention is to provide a new sanitary undergarment that helps reduce the chances of leakage of menstrual fluids.

Even still another object of the present invention is to provide a new sanitary undergarment that is easy to remove from the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a schematic front side view of the present invention.

FIG. 3 is a schematic side view of the present invention.

FIG. 4 is a schematic cross sectional view of the present invention taken from line 4—4 on FIG. 1.

DESCRIPTION OF THE PREFERRED EMBODIMENT

Figure 1:
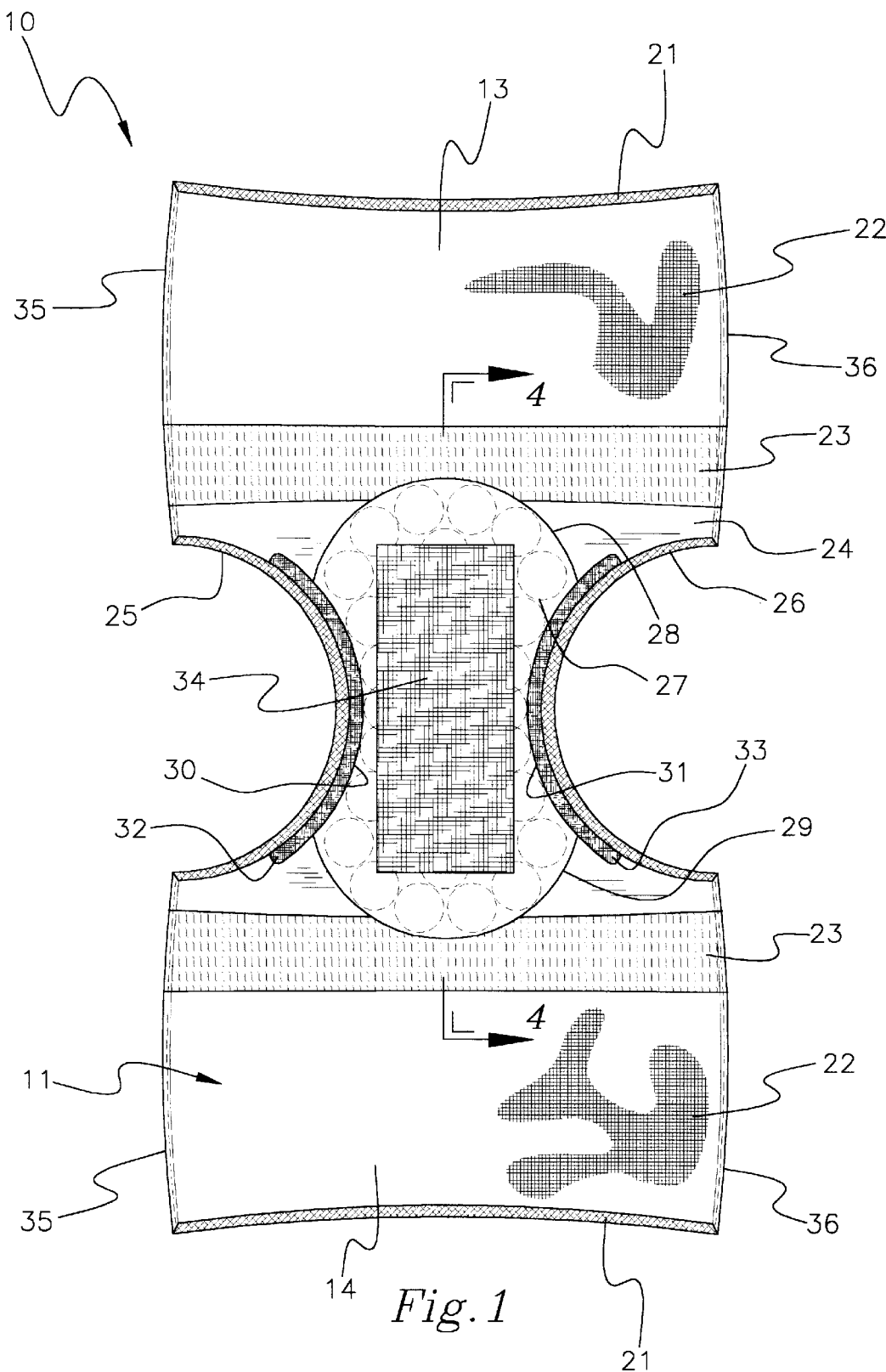
FIG. 1 is a schematic plan view of the inside of a sanitary undergarment separated along the separation lines according to the present invention.

With reference now to the drawings, and in particular to FIGS. 1 through 4 thereof, a new sanitary undergarment embodying the principles and concepts of the present invention will be described.

As best illustrated in FIGS. 1 through 4, the sanitary undergarment comprises an undergarment 10 having front and back portions 13,14, a pair of side portions 15,16, a crotch portion 17, a waist opening 18 and a pair of leg openings 19,20. The undergarment 10 has an upper region 22 extending around the front, back, and side portions 13,14,15,16 of the undergarment 10 adjacent the outer periphery of the waist opening 18. The undergarment 10 also has a middle region 23 extending around the front, back, and side portions 13,14,15,16 of the undergarment 10 adjacent the upper region 22. The middle region 23 comprises a resiliently elastic material adapted for constricting the middle region 23 around a wearer. The undergarment 10 has a lower region 24 beneath the middle region 23 in which the crotch portion 17 and the leg openings 19,20 are located. The lower region 24 comprises a substantially water impermeable material for preventing the passage of menstrual fluids therethrough between the inside 11 and outside 12 of the undergarment 10. The crotch region has a primary absorbing pad 27 on the inside 11 of the undergarment 10.

The undergarment 10 also has a secondary absorbing pad 34 on the primary absorbing pad 27.

In closer detail, the undergarment 10 has an inside 11, an outside 12, front and back portions 13,14, a pair of side portions 15,16, a crotch portion 17, a waist opening 18 and a pair of leg openings 19,20. The crotch portion 17 is positioned between the leg openings 19,20. The waist opening 18 has an outer periphery and each of the leg openings 19,20 also has an outer periphery. The undergarment 10 has an resiliently elastic waist band 21 extending around the outer periphery of the waist opening 18. The waist band 21 is designed for helping hold the undergarment 10 on the waist of a wearer.

The undergarment 10 has an upper region 22 extending around the front, back, and side portions 13,14,15,16 of the undergarment 10 adjacent the outer periphery of the waist opening 18. The upper region 22 has a width defined in a direction extending downwards from the outer periphery of the waist opening 18. The upper region 22 comprises a woven fabric material adapted for permitting the passage of air therethrough between the inside 11 and outside 12 of the undergarment 10 so that the upper garment is breathable when worn to keep the wearer cool.

The undergarment 10 has a middle region 23 extending around the front, back, and side portions 13,14,15,16 of the undergarment 10 adjacent the upper region 22. The middle region 23 comprises a resiliently elastic material adapted for constricting the middle region 23 around a wearer. The middle region 23 has a width defined in a direction extending downwards from the upper region 22. Preferably, the width of the upper region 22 is greater than about twice the width of the middle region 23. Ideally, the width of the upper region 22 is greater than about one-half the distance between the waist opening 18 and one of the leg openings 19,20 along one of the side portions 15,16 of the undergarment 10.

The undergarment 10 additionally has a lower region 24 beneath the middle region 23. The crotch portion 17 and the leg openings 19,20 are located in the lower region 24. The lower region 24 comprises a substantially water impermeable material for preventing the passage and leakage of menstrual fluids therethrough between the inside 11 and outside 12 of the undergarment 10. In use, the middle region 23 constricts the undergarment 10 around the wearer to block leakage of fluids in the lower region 24 up past the middle region 23.

The undergarment 10 has a resiliently elastic leg band 25,26 around the outer perimeter of each of the leg openings 19,20 to help prevent leakage of fluids from the lower region 24 between the legs openings and the legs of a wearer.

The crotch region has a primary absorbing pad 27 on the inside 11 of the undergarment 10. The primary absorbing pad 27 comprises a menstrual fluid absorbing material for absorbing menstrual fluids of a wearer. The primary absorbing pad preferably has convex front and back arcuate ends 28,29 and a pair of concave arcuate sides 30,31. The front and back arcuate ends 28,29 of the primary absorbing pad extending from the lower region 24 into the middle region 23 of the undergarment 10. The arcuate sides 30,31 of the primary absorbing pad 27 are located in the lower region 24 of the undergarment 10. One of the arcuate sides of the primary absorbing pad is positioned adjacent one of the leg openings and the other arcuate side of the primary absorbing pad is positioned adjacent the other leg opening.

Preferably, the undergarment 10 has a pair of arcuate absorbing strips 32,33 on the inside 11 of the undergarment 10. The absorbing strips 32,33 each comprise a menstrual fluid absorbing material. One of the absorbing strips is interposed between one of the leg openings and the adjacent associated arcuate side of the primary absorbing pad. The other absorbing strip is interposed between the other leg opening and the adjacent associated arcuate side of the primary absorbing pad. Preferably, the absorbing strips 32,33 each extend along a semi-circular lower portion of a circumference of the adjacent associated leg opening 19,20. In use, the absorbing strips 32,33 are designed for absorbing menstrual fluid in the lower region 24 that may accumulate near the lower portions of the leg opens thereby helping to prevent menstrual fluid from leaking from around the legs of the wearer.

The undergarment 10 has a secondary absorbing pad 34 on the primary absorbing pad for providing additional absorption of menstrual fluids in area of the crotch most likely needing additional absorption. The secondary absorbing pad 34 also comprises an menstrual fluid absorbing material. Preferably, the secondary absorbing pad 34 is generally rectangular in configuration and has a pair of generally parallel end edges, and a pair of generally parallel side edges extending generally perpendicular to the end edges of the secondary absorbing pad 34. One of the end edges of the secondary absorbing pad 34 is positioned towards the front arcuate end 28 of the primary absorbing pad. Another of the end edges of the secondary absorbing pad 34 is positioned towards the back arcuate end 29 of the primary absorbing pad.

In a preferred embodiment, each of the side portions 15,16 has a separation line 35,36 extending between the waist opening 18 and an adjacent leg opening 19,20. The undergarment 10 is separable along each of the separation lines 35,36 for easy removal of the undergarment 10 from a wearer without the need for the wearer to remove any other exterior clothes. Preferably, the undergarment 10 has a plurality of apertures therein along each of the separation lines 35,36 for aiding separation of the undergarment 10 along the separation lines 35,36. Ideally, the apertures comprise perforations 37 through the undergarment 10 between the inside 11 and outside 12 of the undergarment 10.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An article of clothing, comprising:

an undergarment having an inside, an outside, front and back portions, a pair of side portions, a crotch portion, a waist opening and a pair of leg openings, said crotch portion being positioned between said leg openings;

said waist opening having an outer periphery, each of said leg openings having an outer periphery;

said undergarment having an resiliently elastic waist band extending around said outer periphery of said waist opening, said waist band being for helping hold the undergarment on a waist of a wearer;

said undergarment having an upper region extending around said front, back, and side portions of said undergarment adjacent said outer periphery of said waist opening;

said upper region having a width defined in a direction extending downwards from said outer periphery of said waist opening;

said upper region comprising a woven fabric material adapted for permitting the passage of air therethrough between said inside and outside of said undergarment so that the undergarment is breathable when worn to keep the wearer cool;

said undergarment having a middle region extending around said front, back, and side portions of said undergarment adjacent said upper region;

said middle region having a width defined in a direction extending downwards from said upper region;

said width of said upper region being greater than about twice said width of said middle region, said width of said upper region being greater than about one-half the distance between said waist opening and one of said leg openings along one of said side portions of said undergarment;

said middle region comprising a resiliently elastic material adapted for constricting said middle region around a wearer;

said undergarment having a lower region beneath said middle region, said crotch portion and said leg openings being located in said lower region, said lower region comprising a substantially water impermeable material for preventing the passage of menstrual fluids therethrough between said inside and outside of said undergarment;

said undergarment having a resiliently elastic leg band around the outer perimeter of each of said leg openings to help prevent leakage of fluids between the leg openings and the legs of the wearer;

said crotch portion having a primary absorbing paid on said inside of said undergarment, said primary absorbing pad comprising a menstrual fluid absorbing material for absorbing menstrual fluids of a wearer;

said primary absorbing pad having convex front and back arcuate ends and a pair of concave arcuate sides;

said front and back arcuate ends of said primary absorbing pad extending from said lower region into said middle region of said undergarment;

said arcuate sides of said primary absorbing pad being located in said lower region of said undergarment, one of said arcuate sides of said primary absorbing pad being positioned adjacent to one of said leg openings, another of said arcuate sides of said primary absorbing pad being positioned adjacent to another of said leg openings;

said undergarment having a pair of arcuate absorbing strips on said inside of said undergarment, said absorbing strips each comprising the menstrual fluid absorbing material;

one of said absorbing strips being interposed between one of said leg openings and the adjacent associated arcuate side of said primary absorbing pad, the other of said absorbing strips being interposed between the other of said leg openings and the adjacent associated arcuate side of said primary absorbing pad;

said absorbing strips each extending along a semi-circular lower portion of a circumference of the adjacent associated leg opening, said absorbing strips being for absorbing menstrual fluid in the lower region that may accumulate near the leg openings thereby helping to prevent menstrual fluid from leaking around the legs of the wearer;

said undergarment having a secondary absorbing pad on said primary absorbing pad for providing additional absorption of menstrual fluids in a crotch portion of the wearer, said secondary absorbing pad comprising a menstrual fluid absorbing material;

said secondary absorbing pad being generally rectangular in configuration and having a pair of generally parallel end edges, and a pair of generally parallel side edges extending generally perpendicular to said end edges of said secondary absorbing pad;

one of said end edges of said secondary absorbing pad being positioned towards said front arcuate end of said primary absorbing pad, another of said end edges of said secondary absorbing pad being positioned towards said back arcuate end of said primary absorbing pad; and each of said side portions having a separation line extending between said waist opening and an adjacent leg opening, said undergarment being separable along each of said separation lines for easy removal of said undergarment from the wearer without the need for the wearer to slip an entire leg of the wearer through said leg opening of the article of clothing, wherein said undergarment has a plurality of apertures therein along each of said separation lines for aiding separation of said undergarment along said separation lines, wherein said apertures comprise perforations through said undergarment between said inside and outside of said undergarment.

* * * * *